United States Patent
Tatani et al.

[11] Patent Number: 5,295,400
[45] Date of Patent: Mar. 22, 1994

[54] SLURRY SAMPLING DEVICE AND METHOD

[75] Inventors: Atsushi Tatani; Naohiko Ukawa; Susumu Okino; Toru Takashina; Tsumoru Nakamura, all of Hiroshima; Tokuma Arai, Tokyo; Yoshihiro Shiraishi, Hiroshima, all of Japan

[73] Assignee: Mitsubishi Jukogyo Kabushiki Kaisha, Tokyo, Japan

[21] Appl. No.: 779,189

[22] Filed: Oct. 22, 1991

[30] Foreign Application Priority Data

Oct. 24, 1990 [JP] Japan .................. 2-110481

[51] Int. Cl.$^5$ .................................... G01N 1/10
[52] U.S. Cl. .................................... 73/863.73
[58] Field of Search ........... 73/863.72, 863.75, 864.83, 73/864.84, 64.56

[56] References Cited

U.S. PATENT DOCUMENTS

| | | | |
|---|---|---|---|
| 3,762,609 | 10/1973 | Hagan et al. | 222/636 |
| 4,068,528 | 1/1978 | Gundelfinger | 73/864.84 |
| 4,152,391 | 5/1979 | Cabrera | 73/864.83 X |
| 4,167,117 | 9/1979 | Stokley et al. | 73/863.61 X |
| 4,346,610 | 8/1982 | Ishii et al. | 73/863.73 |
| 4,444,066 | 4/1984 | Ogle et al. | 73/863.72 |
| 4,506,558 | 3/1985 | Bakalyar | 73/863.72 |
| 4,702,889 | 10/1987 | Cabrera et al. | 73/863.73 X |
| 4,823,622 | 4/1989 | Nohl et al. | 73/864.22 X |
| 4,876,902 | 10/1989 | von Alfthan et al. | 73/863.83 |
| 4,948,565 | 8/1990 | Bemis et al. | 73/863.73 X |
| 4,957,008 | 9/1990 | Proni et al. | 73/863.73 X |

FOREIGN PATENT DOCUMENTS

| | | |
|---|---|---|
| 0019052 | 11/1980 | European Pat. Off. . |
| 2141877 | 1/1973 | France . |
| 2250111 | 5/1975 | France . |
| 5080 | 2/1972 | Japan ............ 73/863.72 |
| 855234 | 11/1960 | United Kingdom ......... 73/864.83 |

Primary Examiner—Tom Noland
Attorney, Agent, or Firm—Jacobson, Price, Holman & Stern

[57] ABSTRACT

A slurry sampling device (3) for sampling a slurry in which solid particles are dispersed has upper and lower blocks (105, 109), and a rotator (102) for collection which is rotatably held between the blocks and has a plurality of through holes (111) each having a volume corresponding to the amount of sample to be collected. The upper and lower blocks are provided with slurry conduits (101, 108) and carrier fluid conduits (107, 110) which can be communicated with the through holes so that slurry and carrier fluid can flow therethrough. Arc-shaped long grooves (113, 114) are provided on portions of the upper and lower blocks where ends of the slurry conduits (101, 108) come into contact with, or are adjacent to, the rotator, so that at least one of the through holes is thereby constantly in contact with the long grooves. In the method for sampling slurry a part of the slurry is pumped (2) from a slurry tank (1) and returned (4) to the slurry tank, and that part of the slurry is sampled intermittently by the sampling device (3) and sent to an analyzer (6) for analysis of the composition of the slurry.

14 Claims, 3 Drawing Sheets

SLURRY SAMPLING DEVICE AND METHOD

BACKGROUND OF THE INVENTION

The present invention relates to a device for sampling for analysis a liquid in which precipitating solid particles are suspended (hereinafter referred to as a slurry) and which is kept in a column or tank of an exhaust gas cleaning apparatus or waste water treating apparatus or the like which uses such slurry, and to a method for sampling such slurry for analysis.

A wet lime exhaust gas desulfurizer functions to clean an exhaust gas containing $SO_2$ or the like, such as boiler exhaust gas, through desulfurization with a slurry which is formed by suspending, for example, fine particles of limestone into water and which is kept in a column or tank.

The analysis for the composition of the slurry in such an apparatus has been carried out by quantitative and manual sampling of a small amount of sample required for the analysis with a pipet, and pouring it into an analyzer.

To automate the analysis, there has been adopted such a system as illustrated in FIG. 3, in which liquid in a column or tank 9 is collected through a tube by means of a quantitative semimicropump 8, and quantitatively transferred into an analyzer 6. When an object to be collected is clarified liquid, the above system does not cause any trouble.

However, if an object to be collected is a slurry in which precipitating solid particles are suspended, some solid particles precipitate and deposit in the sampling system, so that the following troubles have conventionally been observed:

1) Analytical accuracy deteriorates;
2) Stable and continuous analysis over a long period of time is impossible due to the clogging of pipes;
3) As a result, analytical data cannot be utilized for process control during the operation of an apparatus; and
4) Maintenance is troublesome.

BRIEF SUMMARY OF THE INVENTION

The purpose of the present invention is to solve the above problems and provide an automatic sampling device and a method for sampling capable of preventing solid particles from precipitating and sedimenting when the slurry is sampled from a column or tank in an "on-line" fashion, so that stable feed of the slurry into an analyzer becomes possible over a long period of time, and so that composition data on the slurry can be obtained and utilized for controlling the slurry composition or for use as control signals.

The present invention provides a slurry sampling device for sampling a slurry in which solid particles are dispersed, which is characterized in that the device comprises an upper block and a lower block, a rotator for collection which is rotatably held between the blocks, the rotator being provided with a plurality of through holes having a volume corresponding to the amount of sample to be collected. The upper and lower blocks are provided with a slurry conduit and a carrier conduit which can be communicated with the through holes so that slurry and carrier fluid can flow therethrough. Arc-shaped long grooves are provided on portions of the upper and lower blocks where an end of the slurry conduit comes into contact with the rotator so that at least one of the through holes is thereby constantly in contact with the long grooves.

The present invention also provides a method for sampling slurry in which a part of the slurry is partially bypassed from a slurry tank and returned to the slurry tank, and the slurry is sampled intermittently from a bypassing line for the partially bypassed slurry and sent to an analyzer for analyzing the composition of the slurry.

According to the present invention, a small amount of sample for the analysis of a slurry can be automatically obtained with stability over a long period of time.

BRIEF DESCRIPTION OF THE DRAWINGS

The invention will now be described in detail with reference to the accompanying drawings wherein:

FIG. 1(b) is a cross sectional view of the device of FIG. 1a;

DETAILED DESCRIPTION OF PREFERRED EMBODIMENTS

Figure 1A:
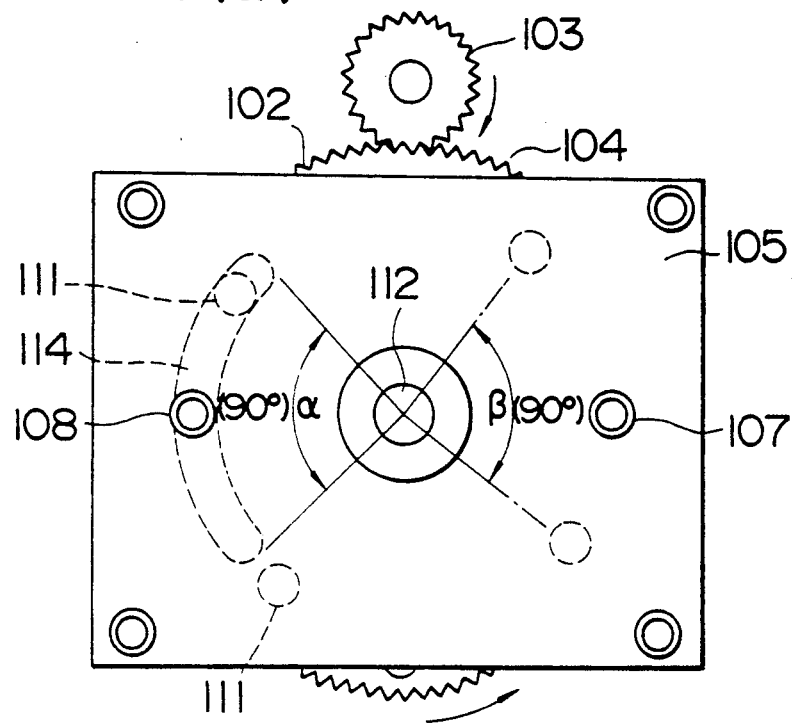
FIG. 1(a) is a schematic top plan view of a sampling device according to one embodiment of the present invention.
Figure 1B:
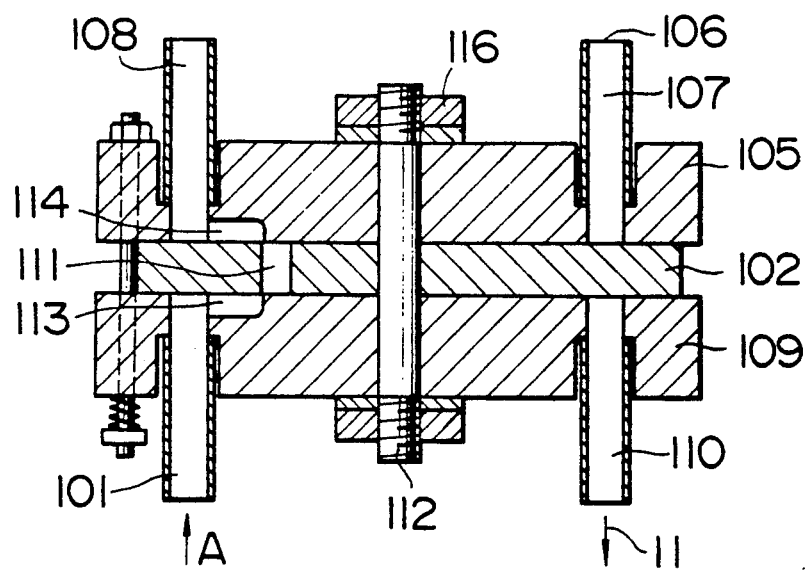
Figure 2:
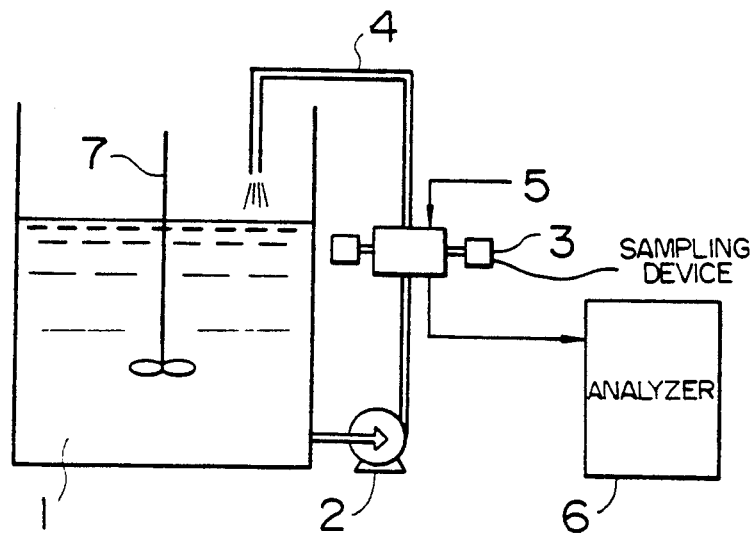
FIG. 2 is a schematic elevational view of a flow circuit showing an embodiment of the present invention.
Figure 3:
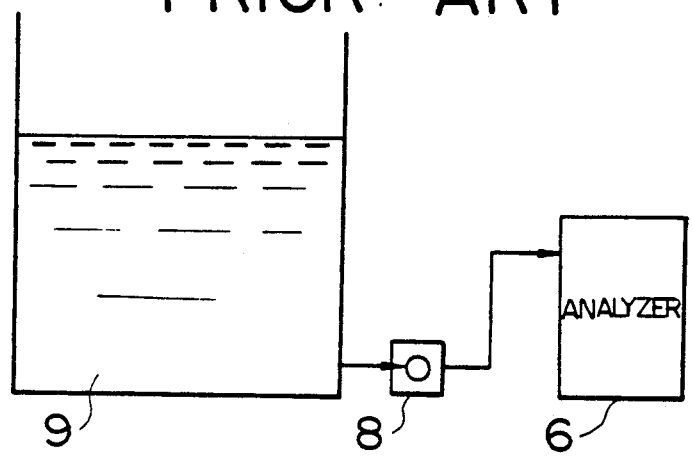
FIG. 3 is a view similar to FIG. 2 showing a conventional embodiment.

FIGS. 1 (a) and (b) illustrate an embodiment of the automatic sampling device of the present invention, and FIG. 2 illustrates a flow circuit of the invention in which slurry kept in a tank is sampled by an automatic sampling device and the sample thus obtained is introduced into an analyzer. First, as shown in FIG. 2, slurry kept in a slurry tank 1 is sampled by a slurry pump 2 and transferred to an automatic sampling device 3. The amount of the slurry forwarded by the slurry pump 2 is overwhelmingly larger than that required for the analyzer, so that most of the slurry is continuously returned to the slurry tank 1 through a return pipe 4. Accordingly, the slurry is transferred as a uniformly dispersed slurry without precipitation and sedimentation of the solid particles in the slurry.

On the other hand, a small amount of the slurry collected by the automatic sampling device 3 is conducted to an analyzer 6. Reference numeral 7 indicates a stirrer.

In the following, the constitution and function of the automatic sampling device of this embodiment will be explained.

As shown in FIG. 1(b), a slurry introducing pipe 101 provided in the main body of the sampling device is connected to a conduit for the slurry forwarded by the slurry pump 2 in FIG. 2, as indicated by the arrow A. The slurry flows into the main body from the lower part thereof for the removal of air bubbles in order to prevent precipitation in the slurry.

Inside the main body, a slurry sampling rotator 102 is provided between an upper block 105 and a lower block 109. The slurry sampling rotator 102 can be rotated by a driving gear 103 which is rotated in turn by an external motor (not shown) and through a rotation gear 104 fitted to the outer circumference of the slurry sampling rotator 102. A carrier introducing pipe 107 for the introduction of a carrier fluid 106 for analysis and a slurry discharging pipe 108 are connected to the upper block 105 of the main body. A carrier exhausting pipe 110 for exhausting a mixture 11 of the carrier fluid and a sample liquid for analysis, and the slurry introducing pipe 101 are connected to the lower block 109 of the main body.

The rotator 102 for the collection of samples has a plurality of through holes 111, and is held between the upper block 105 and the lower bock 109, and can be rotated around a rotation axis 112. Reference numeral 116 indicates a fixing nut for the rotation axis 112.

Also, the slurry introducing pipe 101 and the slurry exhausting pipe 108, as well as the carrier introducing pipe 107 and the carrier exhausting pipe 110, are arranged on vertical straight lines, respectively.

Figure 4:
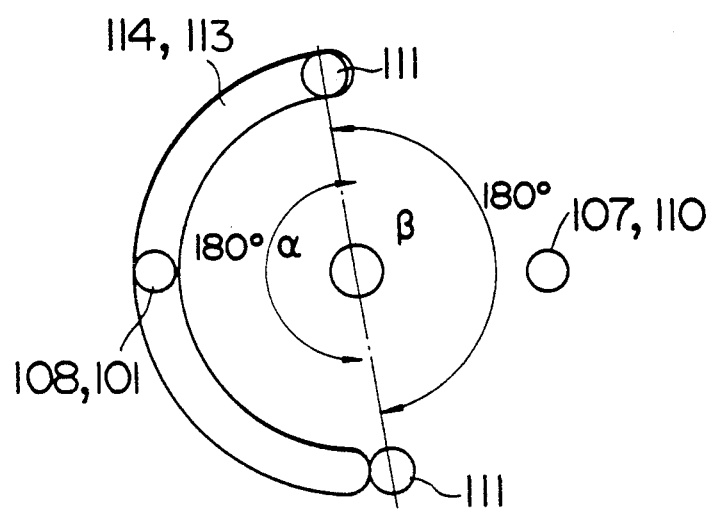
FIG. 4 is a schematic partial plan view showing the operation of a rotator with two through holes for collection according to the present invention.
Figure 5:
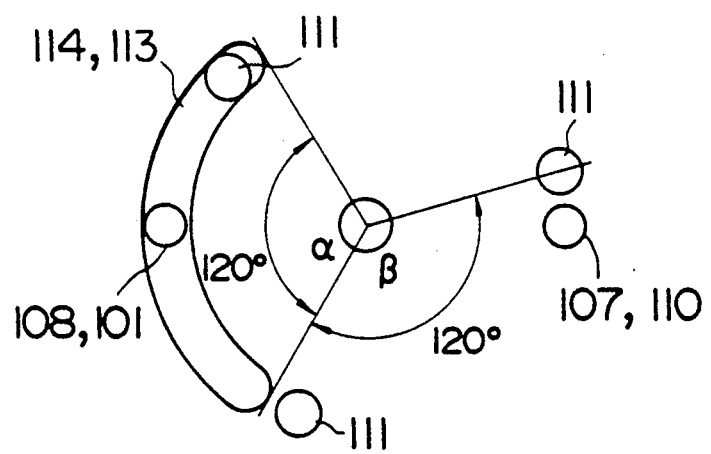
FIG. 5 is a view similar to FIG. 4 showing the operation of a rotator with three through holes for collection according to the present invention.

In addition, a slurry inlet long groove 113 is provided on the inner surface of lower block 109 adjacent rotator 102 where the opening of the slurry introducing pipe 101 in the lower block 109 comes into contact with the rotator 102 for the collection of samples, and a slurry outlet long groove 114 is provided on the inner surface of upper block 105 adjacent votator 102 where the opening of the slurry exhausting pipe 108 of the main body of the upper block 105 comes into contact with the rotator 102, so that these long grooves are symmetrical with respect to each other and rotator 102 for the collection of samples. In the long groove 114, the long groove angle $\alpha$ subtending the ends of the groove is set to be identical with the angle $\beta$ between through holes, so that one of the through holes 111 is always within the range of the long grooves. Furthermore, the long grooves 113 and 114 are provided in the half portions on the side of the slurry inlet and outlet, if two or three through holes are provided as shown in FIGS. 4 and 5.

When the rotator 102 for the collection of samples is rotated to reach the position where the through holes 111 are brought into contact with the slurry inlet long groove 113, the slurry fed to the automatic sampling device flows out through the through holes 111 and the slurry outlet long groove 114 and the slurry exhausting pipe 108.

Next, when the rotator 102 for the collection of sample is rotated to reach the position where one of the through holes 111 and the carrier introducing pipe 107 and the carrier exhausting pipe 110 are fully communicated with each other, the slurry stored in the through holes 111 is carried by an analytical carrier fluid to the analyzer 6 through the carrier fluid exhausting pipe 110.

At that time, since a plurality of the through holes 111 are provided in the rotator 102 for the collection of samples so that another through hole 111 is always within the regions of the slurry inlet long groove 113 and the slurry outlet long groove 114, the slurry forwarded by the slurry pump 2 flows through the return pipe 4 without stagnation. It becomes thus possible to prevent the solid particles in the slurry from precipitating or depositing.

The rotator 102 for the collection of samples may comprise a plurality of through holes 111 which are suitably arranged, and an angle between the through holes should be set to a suitable value. For example, the rotator may have at least two through holes as shown in FIG. 4, and three through holes as shown in FIG. 5.

Thus, while a large quantity of slurry constantly flows because of the slurry pump 2, a small quantity of slurry for analysis can be automatically sampled continuously and stably for a long period of time by the rotation of the rotator 102 for the collection of samples.

Also, it is preferable to set the flow rate of the slurry, which flows through the slurry inlet long groove 113 and the through holes 111 and the slurry outlet long groove 114 and the slurry exhausting pipe 108 via the slurry introducing pipe 101, to a flow rate value of 0.2 m/sec or more, so that the precipitation and deposition of the solid particles may be prevented.

Using the sampling device shown in FIG. 1, continuous automatic analysis of absorbent slurry in a wet type exhaust gas desulfurizer was carried out.

When desulfurization is carried out with a slurry formed by suspending pulverized limestone particles in water by bringing the slurry into gas-liquid contact with an exhaust gas containing $SO_2$, it is essential to control and maintain the concentration of the limestone particles (calcium carbonate: $CaCO_3$) at a predetermined value in operating the wet type exhaust gas desulfurizer.

As shown in FIG. 2, the slurry was automatically sampled from the slurry tank 1 containing the absorbent slurry through the slurry pump 2 by means of the automatic sampling device 3, and the excess amount of the slurry was returned to the slurry tank 1 through the return pipe 4. Simultaneously, the collected sample was forwarded to the carbonate analyzer 6 together with the analytical carrier fluid 5, and the concentration of $CaCO_3$ particles contained in the absorbent slurry could be detected stably and with high accuracy over a long period of time. Using the signals thus obtained for the process control of the exhaust gas desulfurizer, it was possible to obtain excellent operation results without troubles.

We claim:

1. A slurry sampling device for sampling a slurry in which solid particles are dispersed, comprising:
    an upper block and a lower block in relative spaced relationship to provide a space therebetween;
    a rotator for collecting samples rotatably mounted in said space between said blocks;
    a plurality of through holes in said rotator each having a volume corresponding to the amount of sample to be collected;
    slurry conduit means in said upper and lower blocks having inner ends contacting said rotator for selective communication with said through holes to facilitate flow of slurry through said slurry conduit means;
    carrier fluid conduit means in said upper and lower blocks having inner ends contacting said rotator for selective communication with said through holes to facilitate flow of carrier fluid through said carrier fluid conduit means; and
    arc-shaped grooves on portions of said upper and lower blocks communicating with said slurry conduit means where said inner ends of said slurry conduit means contact said rotator so that rotation of said rotator alternately connects at least one of said through holes with said slurry conduit means through said arc-shaped grooves and with said inner ends of said carrier fluid conduit means for transferring a sample from said slurry conduit means to said carrier fluid conduit means, and at all times at least one of said through holes is in contact with said grooves.

2. The slurry sampling device as claimed in claim 1 wherein:
    said rotator has sides facing in opposite directions;

each of said upper and lower blocks has an inner side contacting a respective one of said sides of said rotator;

said arc-shaped grooves comprise an inlet groove on said lower block and an outlet groove on said upper block;

said slurry conduit means comprise a slurry inlet pipe extending through said lower block and communicating with said inlet groove and an outlet pipe extending through said upper block and communicating with said outlet groove; and said carrier fluid conduit means comprise a carrier fluid inlet pipe extending through said upper block and a carrier fluid outlet pipe extending through said lower block.

3. A slurry sampling device as claimed in claim 2 wherein:

said rotator has an axis of rotation;

said arc-shaped grooves and said through holes have substantially the same radius from said axis of rotation so that said through holes communicate with said grooves for the entire length of said grooves when said rotator is rotated;

said grooves have ends defining the arcuate length of said grooves and said arcuate length is substantially the same as the circumferential distance between any two adjacent through holes of said plurality of through holes measured along the path of travel of said through holes about said axis of rotation of said rotator.

4. The slurry sampling device as claimed in claim 3 and further comprising: rotator gear means on said rotator; and drive gear means engaging said rotator gear means for rotating said rotator.

5. The slurry sampling device as claimed in claim 4 wherein:

said rotator comprises a substantially disc shaped member having an outer peripheral surface; and said rotator gear is on said outer peripheral surface of said rotator.

6. The slurry sampling device as claimed in claim 5 wherein:

said plurality of through holes comprises two through holes circumferentially spaced at 180° with respect to each other.

7. The slurry sampling device as claimed in claim 5 wherein:

said plurality of through holes comprises three through holes circumferentially spaced at 120° with respect to each other.

8. A slurry sampling device as claimed in claim 1 wherein:

said rotator has an axis of rotation;

said arc-shaped grooves and said through holes have substantially the same radius from said axis of rotation so that said through holes communicate with said grooves for the entire length of said grooves when said rotator is rotated;

said grooves have ends defining the arcuate length of said grooves; and said arcuate length is substantially the same as the circumferential distance between any two adjacent through holes of said plurality of through holes measured along the path of travel of said through holes about said axis of rotation of said rotator.

9. The slurry sampling device as claimed in claim 1 and further comprising:

rotator gear means on said rotator; and drive gear means engaging said rotator gear means for rotating said rotator.

10. The slurry sampling device as claimed in claim 9 wherein:

said rotator comprises a substantially disc shaped member having an outer peripheral surface; and said rotator gear is on said outer peripheral surface of said rotator.

11. The slurry sampling device as claimed in claim 1 wherein:

said plurality of through holes comprises two through holes circumferentially spaced at 180° with respect to each other.

12. The slurry sampling device as claimed in claim 1 wherein:

said plurality of through holes comprises three through holes circumferentially spaced at 120° with respect to each other.

13. The slurry sampling device as claimed in claim 1 wherein:

said plurality of through holes comprises four through holes circumferentially spaced at 90° with respect to each other.

14. The slurry sampling device as claimed in claim 1 wherein:

said plurality of through holes comprises four through holes circumferentially spaced at 90° with respect to each other.

* * * * *